United States Patent [19]

Vadher

[11] Patent Number: 4,994,042
[45] Date of Patent: Feb. 19, 1991

[54] COMBINED CATHETER & NEEDLE

[76] Inventor: Dinesh L. Vadher, St. Johns Medical Arts Bldg., Rte 25A, Smithtown, N.Y. 11787

[21] Appl. No.: 415,876

[22] Filed: Oct. 2, 1989

[51] Int. Cl.5 ............................................. A61M 5/32
[52] U.S. Cl. ............................ 604/165; 604/164; 604/198; 604/110; 604/263
[58] Field of Search ............... 604/164, 165, 168, 198, 604/263, 110

[56] References Cited

U.S. PATENT DOCUMENTS

| | | |
|---|---|---|
| 3,094,122 | 6/1963 | Gauthier et al. . |
| 3,884,230 | 5/1975 | Wulff . |
| 4,311,137 | 1/1982 | Gerard . |
| 4,389,210 | 6/1983 | Genese . |
| 4,496,348 | 1/1985 | Genese et al. . |
| 4,565,545 | 1/1986 | Suzuki . |
| 4,588,398 | 5/1986 | Daugherty et al. . |
| 4,627,841 | 12/1986 | Dorr . |
| 4,629,450 | 12/1986 | Suzuki et al. . |
| 4,664,654 | 5/1987 | Strauss ................. 604/198 |
| 4,728,322 | 3/1988 | Walker et al. . |
| 4,850,561 | 7/1989 | Wanderer et al. ............ 604/164 |

*Primary Examiner*—Stephen C. Pellegrino
*Attorney, Agent, or Firm*—Leonard Belkin

[57] ABSTRACT

A combined needle and catheter assembly comprising a body in which is provided a plunger having the needle at one end with the catheter enclosing said needle with the tip exposed. A pusher is provided to move the plunger to the proximate end of the body to expose the needle with catheter and to lock the plunger in place against a spring which biases the plunger toward the distal position in the body. After use of the needle with the catheter moved into place, a release is employed to permit the plunger with needle to be driven back into the body, permitting the catheter to be separated from the body and ready for use.

15 Claims, 3 Drawing Sheets

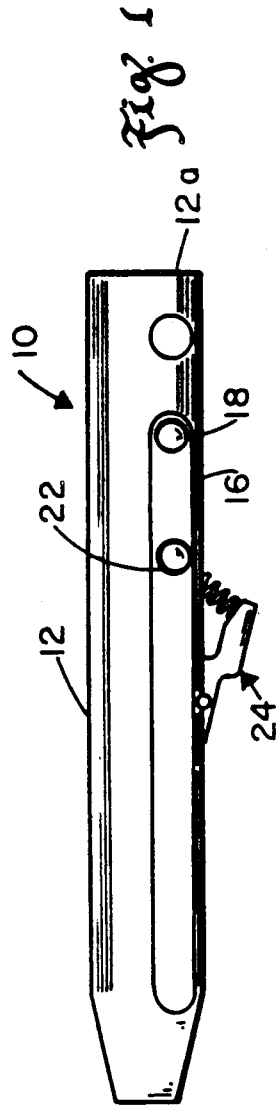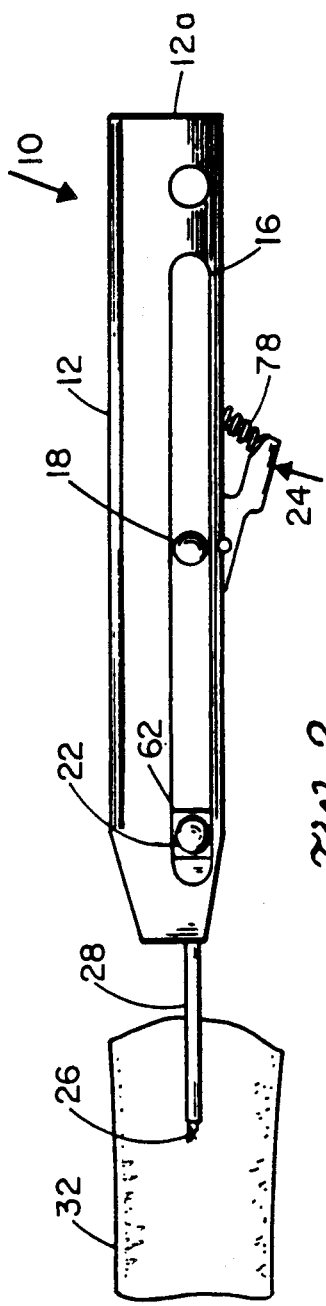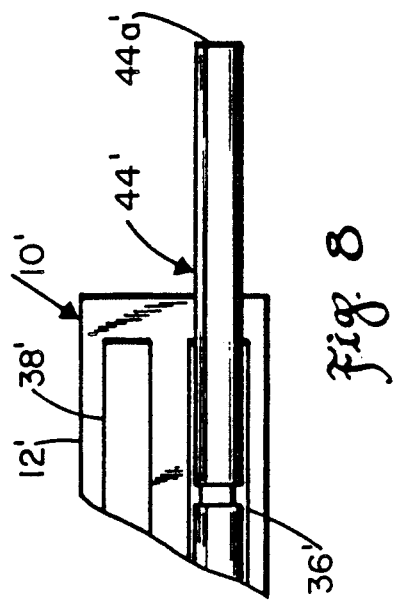

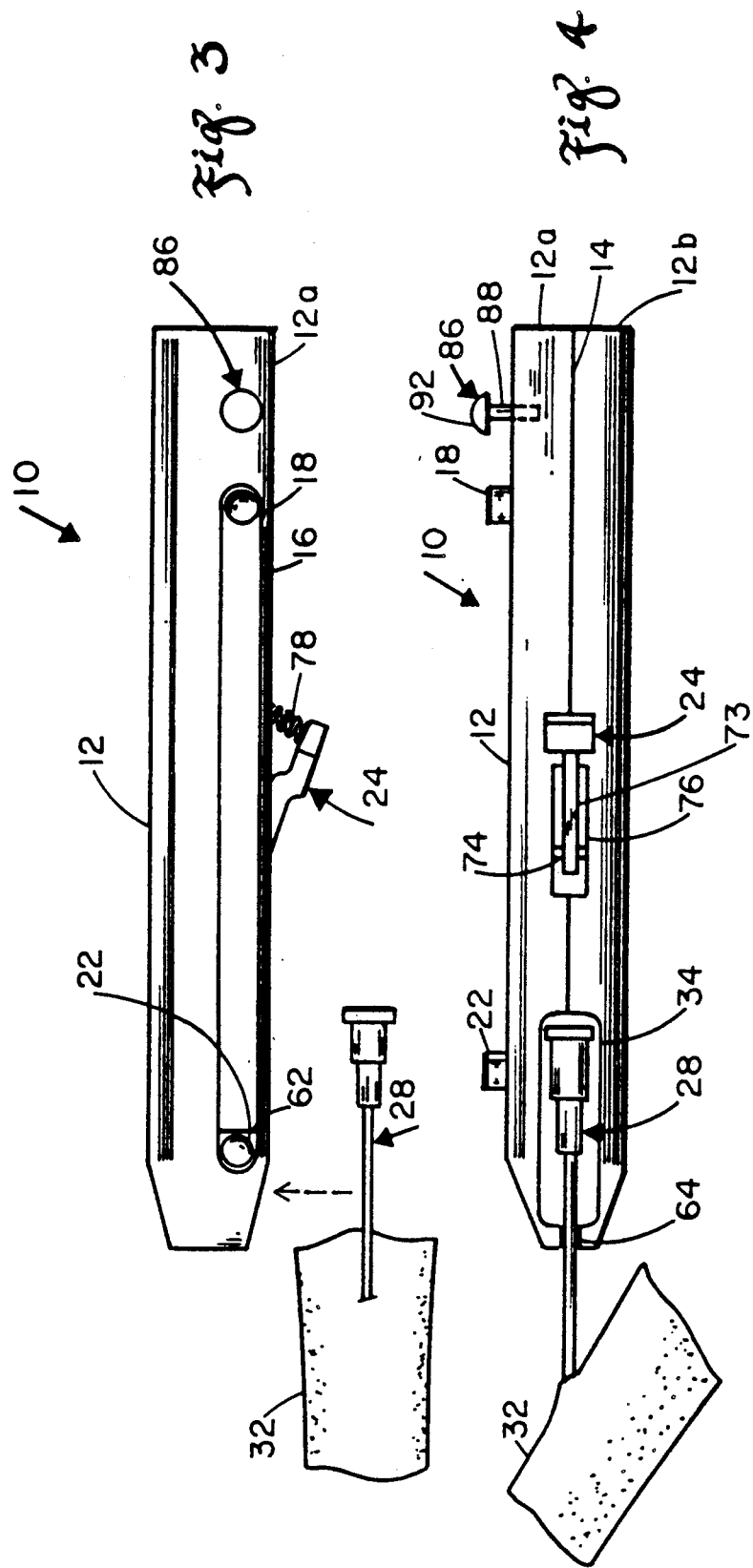

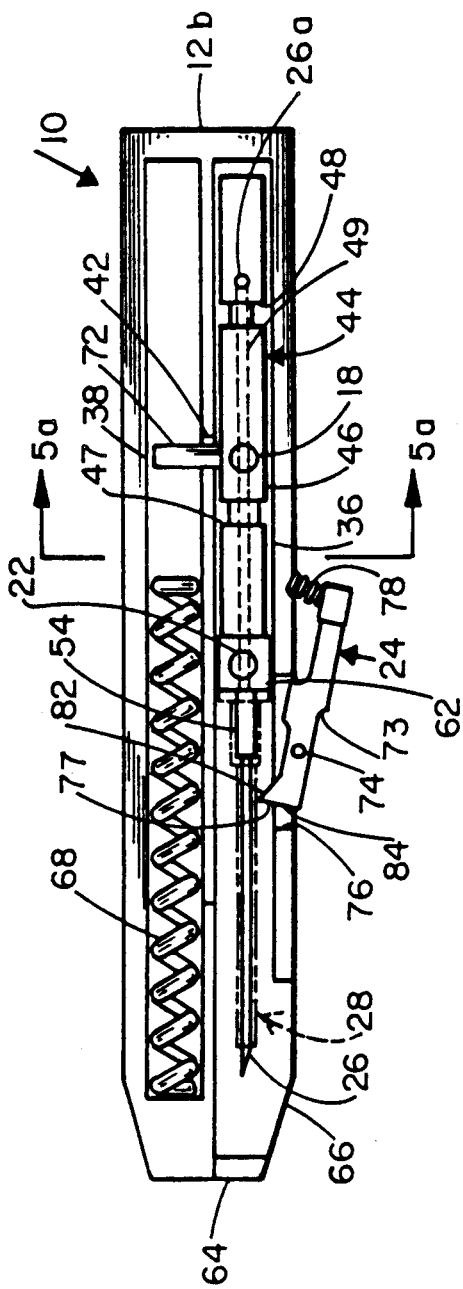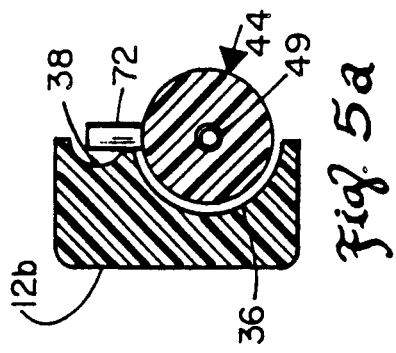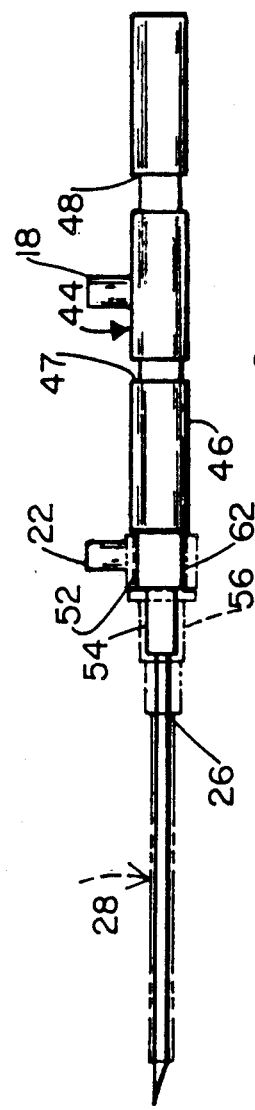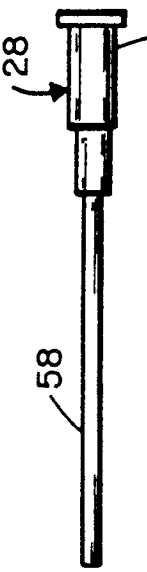

COMBINED CATHETER & NEEDLE

BACKGROUND OF THE INVENTION

The present invention relates to a combined catheter and needle and more particularly to a combined catheter and needle which provides for the disposition of the needle in in a safe manner.

The currently available catheter and needle assembly consists of a needle mounted inside of the catheter sealed and sterile within a package. In the use of such an assembly, the latter is removed from the packaging and the tip of the needle is inserted into the blood vessel through the skin of the patient. When it is seen that a drop of blood comes out of the opposite end of the needle, the medical worker slides the tip of the catheter over the tip of the needle into the blood vessel.

While holding the catheter in place with one hand, the other hand is used to withdraw the needle. The needle has to be dropped in order to attach the I.V. tubing to the catheter. This is the time when most needle punctures occur. Even though hospitals and other institutions have attempted to reduce the risk by providing a disposal unit in each patients room, the distance from the patient to the unit mounted on a wall is not close enough to permit the medical worket to place the used needle in the container while the patient is being attended to.

In the procedure just described, the needle, tipped in the blood of the patient, must be handled until it is deposited in the disposal unit, with the risk of an accidental puncture of one of the health care workers. The risk is heightened in a crisis atmosphere where the patient is undergoing emergency treatment and the workers are concentrating on the rapid delivery of health care services and failing to take the time to observe the usual safety precautions.

From a practical point of view it is almost impossible to provide the disposal unit at every site where the catheter is or might be used. The only solution to this problem would be to improve such needle devices to incorporating safety features into their design.

In addition, once the needle along with a large number of other used and blood tipped needles are in the container, that container as well as others are handled by a succession of workers until final disposal takes place. Over a period of time there is an incidence, although low, of accidents resulting in accidental punctures. In view of the great risk of AIDS and other highly contagious diseases which are transmitted through the blood, the risk described above though low is still unacceptable.

A number of catheter and needle assemblies are shown in USP Nos. 3,094,122, 3,884,230, 4,311,137, 4,389,210, 4,496,348, 4,565,545, 4,588,398, 4,627,841, 4,629,450, and 4,728,322. None of the preceding patents discloses an arrangement for disposing of the needle automatically after the catheter is put in place.

SUMMARY OF THE INVENTION

In this invention the problems described above are largely overcome by providing a catheter and needle assembly in which the needle is automatically sheathed after the catheter is set in place, and the needle remains safely stored with the tip enclosed until finally disposed of.

In accordance with a preferred embodiment of this invention, there is provided a housing containing a slidable plunger from one end of which extends the needle and configured to receive the catheter to enclose the needle with the tip of the needle exposed. The plunger with needle in its initial state is completely contained within the housing. The plunger is provided with a push rod extending out of the housing through a slot extending the length of the housing. The plunger is pushed in the direction of the needle against a spring within the housing until the end of the catheter with the tip of needle is exposed out of the housing. A needle catch engages and holds the plunger in place with the catheter and needle exposed.

The health care professional inserts the needle into the blood vessel of the patient, and after this is verified by the presence of a drop of blood at the opposite end of the needle, the catheter is slid into the opening over the needle using a pusher and then put in place and taped to the skin of the patient. The needle catch is then released, permitting the spring within the housing to retract the needle into the housing where it remains in place. The housing is provided with an opening to permit separation from the catheter left in place and the whole assembly, less the catheter, is disposed of. The housing may be provided with a safety catch which when pressed locks the plunger with needle in place within the housing. The safety catch is designed to be irreversible to prevent inadvertent removal.

The housing with the needle and catheter enclosed is a relatively simple and inexpensive arrangement for delivering a catheter for use and at the same providing for the safe disposal of the needle.

It is thus a principal object of this invention to provide a catheter delivery system which safely secures the needle after use.

Other objects and advantages of this invention will hereinafter become obvious from the following detailed description of preferred embodiments of this invention.

BRIEF DESCRIPTION OF THE DRAWINGS

FIG. 1 is a side elevation view of a preferred embodiment of this invention with the needle and catheter fully retracted prior to us.

FIG. 2 is a view similar to that of FIG. 1 with the needle and catheter extended and ready for insertion.

FIG. 3 is a view similar to FIG. 2 with the catheter inserted, the needle retracted, and the housing being separated from the catheter.

FIG. 4 is a view looking up at the housing shown in FIG. 3 just prior to separation of the housing from the catheter, with the needle fully retracted.

FIG. 5 is a view similar to that of FIG. 1 with one half of the housing removed showing the needle and catheter retracted prior to use.

FIG. 5a is a view along 5a—5a of FIG. 5.

FIG. 6 is an elevation view of the plunger with the needle.

FIG. 7 is an elevation view of the catheter.

FIG. 8 is a detail of the distal end of the assembly shown in FIG. 5 showing an alternative arrangement for moving the plunger.

DETAILED DESCRIPTION OF THE PREFERRED EMBODIMENT

Referring to FIG. 1–4, safety catheter assembly 10 consists of an elongated housing 12 made up of two parts 12a and 12b parted along line 14 (as seen in FIG. 4), and having a slot 16 along the face of part 12a. If desired, housing 12 may be constructed as a single member.

Visible in FIGS. 1-4 are pushers 18 and 22, and needle catch 24 to be further described.

In FIG. 2, needle 26 sheathed in and having its tip extending out of catheter 28, extends out of housing 12 and is ready to be inserted into the arm 32 of the patient.

In FIGS. 3 and 4 needle 26 has been retracted into housing 12 leaving catheter 28 in place with its tip in the arm 32 of the patient. Housing 12 is moved transversely as shown by the arrows in FIG. 3, permitting catheter 28 to pass out of slotted opening 34 in housing 12.

For the details of construction of assembly 10, reference is made to FIGS. 5, 5a, 6, and 7. It will be seen that housing part 12b is provided with one half of a main central passageway 36 of semi circular cross section and a one half of secondary passageway 38 also of semi circular cross section parallel to and adjacent passageway 36. The two passageways are joined by a slot 42 for a purpose to be later described. Housing part 12b is provided with matching passageways and slot so that when the two parts 12a and 12b are assembled as in FIGS. 1-4, there are two passageways circular in cross section with a slot joining them.

Within main passageway 36 for slideable movement is a plunger 44. The latter consists of a cylindrical barrel 46 with a pair of circular grooves 47 and 48, a passageway 49 connecting needle 26 to a port 26a, and end portions 52 and 54 of reduced diameters the latter of which is to accomodate catheter 28 shown in FIG. 6. Extending from end portion 54 of plunger 44 is hollow needle 26. As seen in FIG. 5, catheter 28 (shown in phantom for illustrative purposes) encloses needle 26 with the adaptor 56 portion of catheter 28 fitting over end portion 54 of plunger 44, and the tip of needle 26 exposed from the end of the body 58 of catheter 28.

A floating cylindrical ring 62 rides over end portion 52 of plunger 44 thus filling the space between the right end of catheter 28 and the left end of cylindrical barrel 46 when the catheter and the plunger are assembled within housing 12 as illustrated in FIGS. 5 and 6. Ring 62 and barrel 46 are provided with push rods 22 and 18, respectively, previously identified, extending out of slot 16 in housing part 12a as shown in FIGS. 1, 2, and 3. The left end of housing 12 is provided with a slotted opening 64 which communicates with slotted side opening 34 previously identified. This communication of the two slotted openings 34 and 64 renders corner 66 of housing 12 open to permit catheter 28 to slide out of housing 12 as illustrated in FIGS. 3 and 4.

Mounted within secondary passageway 38 is a spring 68 attached to the left end of passageway 38. Extending into passageway 38 through the slotted opening 42 between the two passageways 36 and 38 is a compression pin 72. When plunger 44 is pushed to the left using push rod 18 as will be explained later, pin 72 will compress spring 68 thereby resulting in plunger 44 being biased to the right.

Housing 12 is also provided with the needle catch 24 which consists of a member 73 pivoted at a pin 74 in a slot 76 also seen in FIG. 4 large enough to accomodate member 73 as is illustrated. At one end, member 73 is provided with a claw 77 extending into passageway 36 through slot 76 while at the other end a spring 78 is provided to bias claw 77 into passageway 36. Claw 77 has a sloped side 82 on the right side and a surface 84 on the left side which is substantially vertical to the axis of plunger 44.

Also provided in housing 12 is a safety catch pin 86 (see FIGS. 3 and 4) located in housing portion 12a aligned with groove 48 with plunger 44 in its position shown in FIG. 5 and normally in the retracted position shown. Catch pin 86 consists of a barrel 88 and a mushroom shaped cap 92. As will be seen below, after assembly 10 has been used and catheter 28 has been removed, and needle 26 retracted into housing 12, catch 86 would be depressed so that the bottom tip of barrel 88 would enter groove 48 and prevent needle 26 from accidentally being extended out of housing 12. Catch pin 86 is designed so that once it is depressed it can no longer be accidentally retracted. This is accomplished by the use of the mushroom shaped cap which does not provide an edge along the surface of housing 12 which can be caught, or it can be slightly countersunk to prevent accidental retraction of the catch. Any other suitable design may be employed if it is desired to make the device tamper proof.

In the operation of the apparatus just described, the combined catheter and needle assembly 10 is delivered ready for use as shown in FIGS. 1 and 5, with needle 26 retracted and catheter 28 covering needle 26 with the tip exposed. The medical professional holds assembly 10 in one hand, and with the other hand slides pusher 18 to the left, moving needle 26 and catheter 28 to become exposed as shown in FIG. 2, compression pin 72 compressing spring 68. The left end of plunger 44 contacting the sloped side 82 of claw 77 raises the latter which drops into groove 47 thereby locking plunger 44 along with needle 26 and catheter 28 in the extended position shown in FIG. 2. It will be noted that floating ring 62 with its pusher 22 extending out of slot 16 will be moved along with plunger 44 and will end up in the position shown also in FIG. 2.

The worker then gently inserts needle 26 into the patient, in this case, for illustrative purposes, arm 32. The presence of a drop of blood coming out of the distal end of needle 26 through port 26a confirms that the needle had entered a blood vessel. The professional then slides the tip of the catheter 28 into the opening of the blood vessel by moving pusher 22 to the left, so that floating ring 62 moves catheter 28. The professional will then hold catheter 28 in place using a thumb or other finger to press catheter 28 against the skin of the patient, and depress member 73 against spring 76, raising claw 77 out of groove 47 thereby releasing plunger 44 which will be pushed back into housing 12 by spring 68, leaving catheter 28 in the position shown in FIG. 4. Then, unit 10 is gently moved transversely as shown in FIG. 3, letting catheter 28 pass through opening 34 and remaining on the arm of the patient. The professional will then adjust catheter into the position desired and tape it down against the arm of the patient. Catheter 28 may then be capped for later use, or the IV can be attached in conventional fashion to adaptor 56 on catheter 28.

Safety pin 88 would then be depressed to enter groove 48 thereby insuring that needle 26 will not be accidentally exposed, and the whole remaining assembly, minus catheter 28, will be deposited in a repository for such used medical equipment for proper disposal.

Instead of employing pusher 18 extending out of slot 16, the arrangement shown in FIG. 8 may be employed to move plunger 44 to the left.

As seen in FIG. 8 assembly 10' otherwise identical to assembly 10 previously described, is provided with a plunger 44' identical to plunger 44 except that pusher 18 is removed and the distal end of plunger 44' is extended to pass out of housing 12' so that the rear end 44a' can be pushed by a finger, for example, to move plunger 44' toward the proximate end of housing 12'.

It is thus seen that there has been provided a unique combination of a needle and catheter in a compact assembly which is convenient to use, is disposable, and at the same time sheaths the needle after use so that there is no risk of accidental puncture afterwards.

While only certain preferred embodiments of the invention has been described it is understood that many variations are possible without departing from the principles of this invention as defined in the claims which follow.

What is claimed is:

1. A combined medical needle and catheter assembly comprising:
    a. an elongated body with a proximate end and a distal end having an extended principal passageway and an extended secondary passageway parallel to and adjacent each other, said passageways being spaced from each other and communicating with each other through an extended slot;
    b. plunger means within said principal passageway slidable along the length of said passageway;
    c. a hollow needle extending from the proximate end of said plunger means fully contained within said principal passageway with said plunger means adjacent the distal end of said body;
    d. spring means mounted within and at the proximate end of said secondary passageway;
    e. compression pin means mounted on said plunger means extending through said extended slot into said secondary passageway for compressing said spring means when said plunger means is moved toward the proximate end of said body;
    f. catheter means enclosing said needle with the tip of the latter extending past the proximate end of said catheter means thereby being exposed;
    g. means for pushing said plunger means to the proximate end of said body, whereby said needle with catheter extend out from the proximate end of said body when said plunger means is at the proximate end of said principal passageway;
    h. means for locking said plunger means in the proximate position with said needle and catheter extended; and
    i. means for releasing said plunger means to permit said spring means to retract said needle back into said body after use leaving said catheter means extending out of said body.

2. The assembly of claim 1 having means to slide said catheter means past the tip of said needle when plunger means is in the proximate end of said body.

3. The assembly of claim 1 having means to lock said plunger means in its distal position after use and retraction of said needle.

4. The assembly of claim 1 having means in said plunger means for indicating the proper positioning of said needle.

5. The assembly of claim 4 wherein said indicating means includes a port in said plunger means communicating with said needle.

6. The assembly of claim 5 wherein said body includes an extended opening to view said port and said pushing means comprises a transversely extended member on said plunger means passing to the outside of said body through said opening to permit said plunger means to be pushed.

7. The assembly of claim 1 wherein said body includes means to permit said catheter and body to be separated after said needle is retracted into said body.

8. The assembly of claim 1 wherein said locking means comprises claw member means pivoted on said body biased into contact with said plunger means so that claw member means engages said plunger means in its proximate position thereby locking said plunger means in position.

9. The assembly of claim 6 wherein said releasing means includes means to effectuate the retraction of said claw means from said plunger means.

10. The assembly of claim 1 wherein said pushing means includes an extension of said plunger means through the distal end of said body.

11. A combined medical needle and catheter assembly comprising:
    a. an elongated body with a proximate end and a distal end having an extended passageway;
    b. plunger means within said passageway slidable along the length of said passageway;
    c. a hollow needle extending from the proximate end of said plunger means fully contained within said passageway when said plunger means is adjacent the distal end of said body;
    d. bias means mounted within said body;
    e. means on said plunger means for contacting said bias means when said plunger means is moved toward the proximate end of said body thereby biasing said plunger means toward the distal end of said body;
    f. catheter means enclosing said needle with the tip of the latter extending past the proximate end of said catheter means thereby being exposed;
    g. means for pushing said plunger means to the proximate end of said body, whereby said needle with catheter extend out from the proximate end of said body when said plunger means is at the proximate end of said passageway;
    h. means for locking said plunger means in the proximate position with said needle and catheter extended; and
    i. said locking means including means for releasing said plunger means to permit said bias means to retract said needle back into said body after use leaving said catheter means extending out of said body.

12. The assembly of claim 11 wherein said assembly includes means to slide said catheter past the tip of said needle when said needle is extended from said body.

13. The assembly of claim 12 wherein said body includes means to permit said catheter and body to be separated after said needle is retracted into said body.

14. The assembly of claim 11 wherein said bias means includes spring means which is compressed as said plunger means is moved into said proximate position.

15. The assembly of claim 11 wherein said locking means comprises means mounted on said body to engage and lock said plunger means when in its proximate position within said body.

* * * * *